US00PP24544P3

(12) United States Plant Patent
Scheffers

(10) Patent No.: US PP24,544 P3
(45) Date of Patent: Jun. 10, 2014

(54) ***DRACAENA* PLANT NAMED 'DRAGONRAYO'**

(50) Latin Name: *Dracaena reflexa*
Varietal Denomination: Dragonrayo

(71) Applicant: Ruud Scheffers, Honselersdijk (NL)

(72) Inventor: Ruud Scheffers, Honselersdijk (NL)

(73) Assignee: DragonTree Beheer (NL)

( * ) Notice: Subject to any disclaimer, the term of this patent is extended or adjusted under 35 U.S.C. 154(b) by 46 days.

(21) Appl. No.: 13/573,681

(22) Filed: Oct. 2, 2012

(65) Prior Publication Data

US 2014/0096298 P1 Apr. 3, 2014

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Kent L Bell
(74) *Attorney, Agent, or Firm* — Cassandra Bright

(57) ABSTRACT

A new and distinct *Dracaena* cultivar named 'Dragonrayo' is disclosed, characterized by dark green leaves, with a high gloss apperance. Plants grow rapidly. The new variety is a *Dracaena*, typically produced as an ornamental plant.

1 Drawing Sheet

Latin name of the genus and species: *Dracaena reflexa.*
Variety denomination: 'Dragonrayo'.

BACKGROUND OF THE INVENTION

The new cultivar is the product of chance discovery. The new variety originated as a naturally occurring whole plant mutation of an unpatented, unnamed variety of *Dracaena reflexa.*

The new variety was discovered by the inventor, Ruud A. M. Scheffers, a citizen of the Netherlands, in 2006 in a commercial greenhouse belonging to the inventor in Honselersdijk, The Netherlands. After identifying the new variety as a potentially interesting selection, the inventor continued confidential testing and propagation of 'Dragonrayo' assessing stability of the unique characteristics of this variety.

Asexual reproduction of the new cultivar 'Dragonrayo' was first performed at the commercial greenhouse of the inventor in Honselersdijk, The Netherlands by vegetative cuttings in 2006. Access to all plants was restricted, as plants were kept in a locked greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar 'Dragonrayo' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Dragonrayo'. These characteristics in combination distinguish 'Dragonrayo' as a new and distinct *Dracaena* cultivar:

1. Glossy dark green foliage.
2. Rapid growth.

PARENT COMPARISON

Plants of the new cultivar 'Dragonrayo' are similar to the parent, an unpatented, unnamed variety of *Dracaena reflexa* in most horticultural characteristics. The new variety, however, produces darker, shinier leaves and grows faster than the parent.

COMMERCIAL COMPARISON

'Dragonrayo' can be compared to the unpatented commercial variety *Dracaena reflexa* 'Anita'. The varieties are similar in most horticultural characteristics, however, 'Dragonrayo' differs from 'Anita' in producing longer, glossier foliage. Additionally, foliage of 'Dragonrayo' grows in a more upright habit than foliage of 'Anita'.

BRIEF DESCRIPTION OF THE PHOTOGRAPH

The accompanying photograph in FIG. 1 illustrates in full color a typical plant of 'Dragonrayo' grown in a commercial greenhouse in Honselersdijk, The Netherlands. This plant is approximately 2 months old, shown planted in a 12 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Dragonrayo' plants grown in a greenhouse in Honselersdijk, The Netherlands. A steady temperature of approximately 20° C. at night and 20° C. during the day was maintained. No artificial light, photoperiodic treatments were given to the plants. Measurements and numerical values represent averages of typical plant types.

Botanical classification: *Dracaena reflexa* 'Dragonrayo'.

PROPAGATION

Time to initiate rooting: About 5 to 6 weeks at approximately 20° C. 6 weeks for full rooting.

Root description: Moderately thick, moderately fibrous, not fleshy, young roots Yellow-White 158D, older roots Greyed-Orange 163C.

PLANT

Age of plant described: 2 months.

Pot size of plant described: 12 cm pot.

Growth habit: Upright.

Height: Approximately 23.8 cm.

Plant spread: Approximately 31.3 cm.

Growth rate: Moderate, approximately 8 cm per month.

Branching characteristics: Not free branching, typically growing with one main stem from the base. Will only develop lateral branches after pinching or pruning.

Diameter of stem: Approximately 1.0 cm.

Length of stem: Approximately 20 cm.

Internode length: Average 0.5 cm.

Texture of stem: Smooth, dull.

Color of stem: A color in between green and yellow-green; near RHS N137A and 146A.

Stem strength: Very strong.

Number of leaves per stem: Average 58.

FOLIAGE

Leaf:

*Arrangement*.—Alternate (spirally).

*Average length*.—Approximately 20.3 cm.

*Average width*.—Approximately 1.2 cm.

*Shape of blade*.—Ensiform.

*Aspect*.—Strongly curved downward.

*Apex*.—Acute.

*Base*.—Broad cuneate.

*Attachment*.—Decurrent.

*Margin*.—Entire.

*Texture of top surface*.—Smooth, very glossy.

*Texture of bottom surface*.—Smooth, very glossy.

*Color*.—Young foliage upper side: Green; near RHS 143A, base Yellow-green; near RHS 145B. Young foliage under side: Yellow-green; near RHS 144A, base lighter, near 144D. Mature foliage upper side: Green; in between near RHS 137A and 141A but darker. Mature foliage under side: Green; near RHS 137B.

*Venation*.—Type: parallel. Color: Upperside: As leaf blade: green; in between near RHS 137A and 141A but darker. Underside: As leaf blade: green; near RHS 137B.

*Sheath*.—Average Length: Approximately 1.1 cm. Average Width: Approximately 1.0 cm. Color: Upper side greyed-green; near RHS 193A, under side yellow-green; 144B. Texture: smooth, upper side glossy, under side dull.

OTHER CHARACTERISTICS

Flower production: Not observed.

Disease resistance: Neither resistance nor susceptibility to normal diseases and pests of *Dracaena* has been observed.

Drought tolerance and temperature tolerance: Moderately high drought resistance, good heat resistance.

Fruit/seed production: Not observed.

What is claimed is:

1. A new and distinct cultivar of *Dracaena* plant named 'Dragonrayo' as herein illustrated and described.

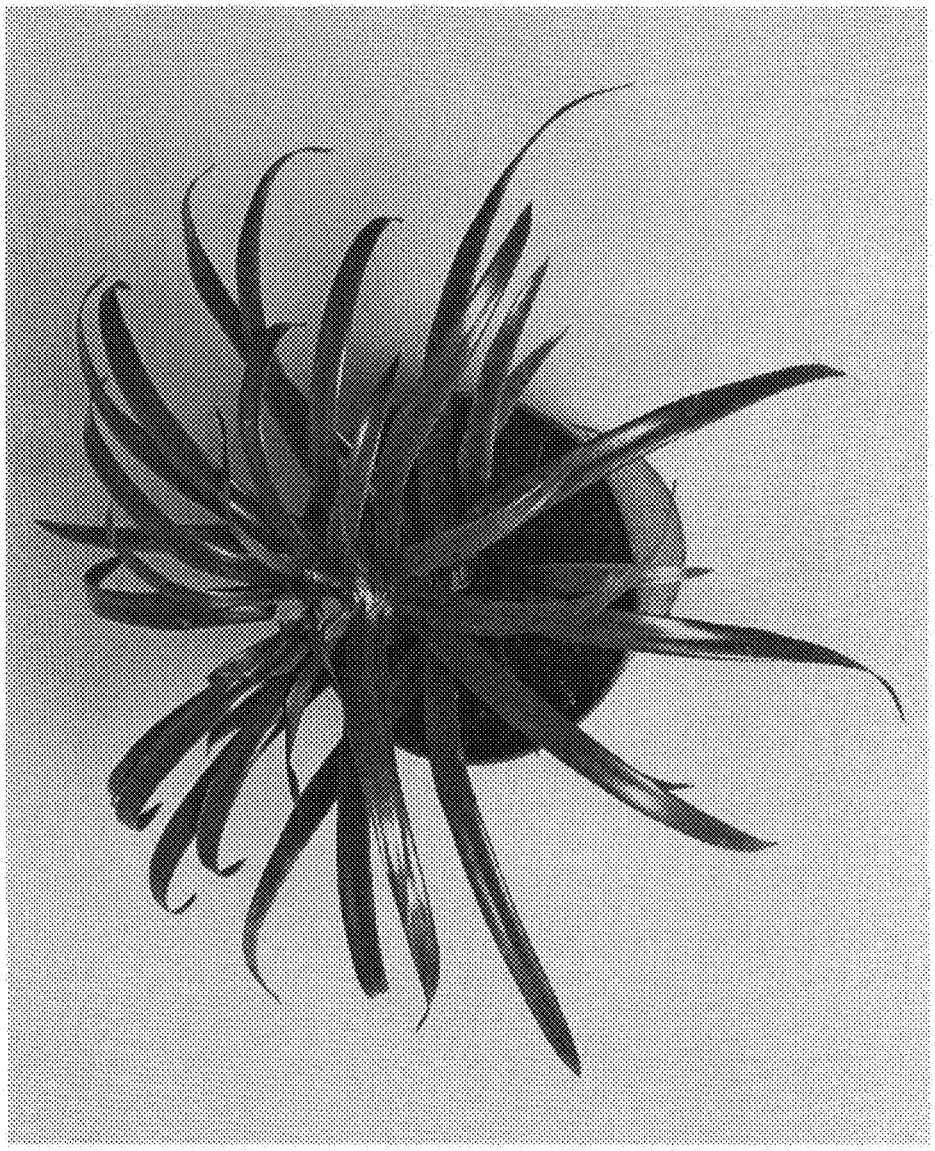

* * * * *